US009895086B2

(12) United States Patent
Van De Laar et al.

(10) Patent No.: US 9,895,086 B2
(45) Date of Patent: Feb. 20, 2018

(54) DEVICE FOR MONITORING A USER AND A METHOD FOR CALIBRATING THE DEVICE

(71) Applicant: KONINKLIJKE PHILIPS N.V., Eindhoven (NL)

(72) Inventors: Jakob Van De Laar, Oosterhout (NL); Haris Duric, Bothell, WA (US); Teun Van Den Heuvel, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 940 days.

(21) Appl. No.: 14/349,671

(22) PCT Filed: Oct. 8, 2012

(86) PCT No.: PCT/IB2012/055425
§ 371 (c)(1),
(2) Date: Apr. 4, 2014

(87) PCT Pub. No.: WO2013/057622
PCT Pub. Date: Apr. 25, 2013

(65) Prior Publication Data
US 2014/0296660 A1 Oct. 2, 2014

Related U.S. Application Data

(60) Provisional application No. 61/547,972, filed on Oct. 17, 2011.

(51) Int. Cl.
*A61B 5/11* (2006.01)
*A61B 5/0205* (2006.01)
(Continued)

(52) U.S. Cl.
CPC .......... *A61B 5/1118* (2013.01); *A61B 5/0205* (2013.01); *A61B 5/1116* (2013.01);
(Continued)

(58) Field of Classification Search
CPC ... A61B 5/1118; A61B 5/0205; A61B 5/1116; A61B 5/024; A61B 5/0816; A61B 2562/0219
See application file for complete search history.

(56) References Cited

U.S. PATENT DOCUMENTS

| 4,846,195 A | 7/1989 | Alt |
| 6,044,297 A | 3/2000 | Sheldon et al. |
| (Continued) | | |

FOREIGN PATENT DOCUMENTS

WO 2004041086 A1 5/2004

OTHER PUBLICATIONS

Roetenberg , Inertial and Magnetic Sensing of Human Motion, 2006, pp. 1-15, 77-83.*

*Primary Examiner* — John Breene
*Assistant Examiner* — Mohammad Islam

(57) ABSTRACT

A method of calibrating a monitoring device to be attached to a user is provided. Prior to attachment of the device, the device is aligned with respect to the user such that the measurement reference frame of the device is substantially aligned with a reference frame of the user. A first measurement of the orientation of the device with respect to a world reference frame is obtained. After attachment of the device, a second measurement of the orientation of the device with respect to a world reference frame is obtained. A transformation matrix is determined for use in transforming subsequent measurements obtained by the device into the reference frame of the user. The matrix is calculated using the first and second measurements and information on the amount of rotation of the device relative to the user about a vertical axis in the world reference frame between the first and second measurements being taken.

18 Claims, 7 Drawing Sheets

(51) Int. Cl.
 *A61B 5/024* (2006.01)
 *A61B 5/08* (2006.01)
(52) U.S. Cl.
 CPC ............ *A61B 5/1121* (2013.01); *A61B 5/024* (2013.01); *A61B 5/0816* (2013.01); *A61B 2560/0223* (2013.01); *A61B 2562/0219* (2013.01)

(56) References Cited

U.S. PATENT DOCUMENTS

| | | | | |
|---|---|---|---|---|
| 2007/0115277 | A1* | 5/2007 | Wang | A61B 5/1116 345/419 |
| 2007/0118056 | A1* | 5/2007 | Wang | A61B 5/1116 600/595 |
| 2011/0173830 | A1* | 7/2011 | Hagino | G01B 5/008 33/553 |
| 2012/0113228 | A1* | 5/2012 | Konno | H04N 13/0452 348/47 |
| 2012/0169716 | A1* | 7/2012 | Mihara | H04N 13/0275 345/419 |
| 2012/0185204 | A1* | 7/2012 | Jallon | G01C 21/16 702/141 |
| 2014/0303524 | A1* | 10/2014 | Chen | A61B 5/11 600/595 |

* cited by examiner

DEVICE FOR MONITORING A USER AND A METHOD FOR CALIBRATING THE DEVICE

CROSS REFERENCE TO RELATED APPLICATIONS

This application is a national filing of PCT application Serial No. PCT/IB2012/055425, filed Oct. 8, 2012, published as WO 2013/057622 A1 on Apr. 25, 2013, which claims the benefit of U.S. provisional application Ser. No. 61/547,972 filed Oct. 17, 2011, which is incorporated herein by reference.

FIELD OF THE INVENTION

The invention relates to a device for monitoring a user and a method for calibrating the device.

BACKGROUND OF THE INVENTION

The application of patient monitoring has been extended into a variety of settings, including traditional Intensive Care Units (ICUs), step-down and medium-care units, medical and surgical care floors, and at home. In many of these settings it is critical to have knowledge of the circumstances under which a set of vital signs has been obtained. One crucial piece of information is the body posture of the monitored user (for example, upright, supine, prone, laying on left side, laying on right side, etc) at the time of monitoring.

In clinical practice, there are many care protocols in place that require patient position to be accurately tracked and recorded in time. Some examples include the protocols of recording vital signs, interpreting Screen TrendsInnovative (ST) maps, preventing pressure ulcers, detecting bed exit, detecting a fall, weaning from mechanical ventilation, pneumonia prevention, etc. Nowadays, miniature patient monitoring devices are available which contain accelerometers that can measure vital signs (such as respiration and pulse rate) and that can, at the same time, measure the inclination of the device based on an observation of gravity. From the sensor signals obtained from these devices and the knowledge of the location and/or orientation of the device with respect to the body of the monitored user, the posture of the user can be estimated and tracked.

When a device is placed on or attached to a user, it is desirable for the measurement reference frame of the accelerometer in the device to be aligned with the reference frame of the body of the user. However, due to the variability in body shapes of users and individual device attachment, there is likely to be some misalignment between these reference frames. To accurately monitor the posture of a user, it is necessary to determine the relative orientation between the measurement reference frame and the reference frame of the body of the user. This relative orientation is illustrated in FIG. 1.

In FIG. 1, $z_b$ represents the z-axis of the reference frame of the user which is aligned normal to the user's body (i.e. it is perpendicular to the plane of the user's back, directed towards the front of the body), $y_b$ represents the y-axis of the reference frame of the user which is aligned substantially vertically upwards towards the head of the user, and $x_b$ represents the x-axis of the reference frame of the user which is orthogonal to the y- and z-axes. Although the device has been placed on or attached to the user in an attempt to align the measurement reference frame of the accelerometer (represented by axes $x_a$, $y_a$ and $z_a$) with the reference frame of the user, it can be seen that, due to the shape of the part of the body to which the device has been attached, the device may have undergone rotation, resulting in a difference or misalignment between the reference frames.

A calibration procedure is therefore required in order to compute this unknown relative orientation, and to allow for accurate posture estimation.

Previously proposed methods for calibration (such as that disclosed in U.S. Pat. No. 6,044,297) require a user to adopt multiple postures in order for an initial state to be recorded. However, in practice, it is often not desirable or even feasible to ask for the cooperation of a user to adopt such a sequence of postures during the calibration procedure because the user may be too unwell, required to remain still for medical reasons, unconscious, etc. Ideally, it should be possible to perform a calibration procedure without any active involvement or support from the user.

SUMMARY OF THE INVENTION

The invention seeks to provide a device for monitoring a user and a method for calibrating the device that can be performed without any active involvement or support from the user being monitored with the device such that accurate readings can be obtained from the device.

This is achieved, according to an aspect of the invention, by a method of calibrating a device that is to be attached to a user and used to monitor the user, the method comprising the steps of: (i) prior to attachment of the device to the user, aligning the device with respect to the user such that the measurement reference frame of the device is substantially aligned with a reference frame of the user and obtaining a first measurement of the orientation of the device with respect to a world reference frame using the device; (ii) after attachment of the device to the user, obtaining a second measurement of the orientation of the device with respect to a world reference frame using the device; and (iii) determining a transformation matrix for use in transforming subsequent measurements obtained by the device into the reference frame of the user, the transformation matrix being calculated using the obtained first and second measurements and information on the amount of rotation of the device relative to the user about a vertical axis in the world reference frame between steps (i) and (ii).

The first and second measurements may comprise measurements of proper acceleration experienced by the device.

The information on the amount of rotation of the device relative to the user about the vertical axis of the world reference frame between steps (i) and (ii) may comprise information on an angle $\varphi_p$ between the projections of a basis vector $\beta_m$ in the reference frame of the user onto a horizontal plane H perpendicular to the direction in which gravity acts and the basis vector $\alpha_p$ in the measurement reference frame of the device onto the horizontal plane H for some $m,p \in \{1, 2, 3\}$, where $\beta_m$ and $\alpha_p$ do not lie in the direction of gravity.

The step of determining a transformation matrix may comprise the steps of:

computing a first coordinate vector d that is orthonormal to the first measurement b;

computing a second coordinate vector f that is orthonormal to b and d;

computing support vectors $s_i$ and radii $r_i$ of the circles $C_1$, $C_2$ and $C_3$ on which the tips of the $\alpha$ basis vectors lie for $i \in \{1, 2, 3\}$;

if $|a_k|=1$ for some $k$ then computing $t_k:=\text{sign}(a_k)b$;

computing the p-th column of the transformation matrix; and computing one or more remaining resolvable angles and the corresponding one or more columns of transformation matrix.

The step of computing one or more remaining resolvable angles and the corresponding one or more columns of the transformation matrix may comprise performing the following steps for $i \in \{1, 2, 3\} \backslash \{p, k\}$ and $j := \{1, 2, 3\} \backslash \{i, p\}$:

computing the Levi-Civita symbol for the triple (p, i, j);

computing the angle $\varphi_i$ between the projections of the basis vector $\alpha_i$ in the measurement reference frame of the device and the basis vector $\beta_m$ in the reference frame of the user onto the plane H; and computing the corresponding column of the transformation matrix.

The method may further comprise the step of estimating the posture of the user, wherein the step of determining the transformation matrix further uses the estimated posture of the user.

The step of estimating the posture of the user may comprise estimating the posture of the user by analysing the first measurement of the orientation of the device with respect to the world reference frame or receiving an input from the user or an operator indicating the posture of the user.

The method may further comprise the step of displaying information associated with the estimated posture of the user for use by the user or an operator in the attachment of the device to the user.

The displayed information may comprise information on permissible rotations of the device between steps (i) and (ii).

The information on the amount of rotation of the device relative to the user about a vertical axis in the world reference frame between steps (i) and (ii) may be assumed based on the estimated posture of the user.

The information on the amount of rotation of the device relative to the user about a vertical axis in the world reference frame between steps (i) and (ii) may be provided by the user or an operator of the device.

According to another aspect of the invention, there is provided a method of monitoring a user, the method comprising the steps of: determining a transformation matrix according to the method of calibrating a device described above; obtaining further measurements using the device; converting the obtained further measurements into the reference frame of the user using the transformation matrix; and processing the converted obtained further measurements to determine at least one of the posture of the user, the movements of the user, the activity of the user, the respiration rate of the user and/or the pulse rate of the user.

According to another aspect of the invention, there is provided a computer program product comprising a plurality of program code portions for carrying out the method of calibrating a device described above when executed by a suitable computer or processor.

According to another aspect of the invention, there is provided a device for monitoring a user, the device being suitable for attachment to a user, the device comprising: a sensor configured to measure accelerations; and a processor for processing the acceleration measurements; wherein the processor is configured such that, when the device is operating in a calibration mode: the processor uses a first acceleration measurement as an indication of the orientation of the reference frame of the user with respect to a world reference frame obtained prior to attachment of the device to the user and a second acceleration measurement as a measurement of the orientation of the device with respect to a world reference frame following attachment of the device to the user, and the processor determines a transformation matrix for use in transforming subsequent acceleration measurements obtained by the device into the reference frame of the user, the transformation matrix being calculated using the obtained first and second measurements and information on the amount of rotation of the device relative to the user about a vertical axis of the world reference frame between the first and second measurements being taken.

The processor may be further configured such that, when the device is operating in a monitoring mode, the processor uses the calculated transformation matrix to convert further acceleration measurements obtained by the sensor into the reference frame of the user.

The processor may be further configured such that, when the device is operating in the monitoring mode, the processor processes the converted further acceleration measurements to determine at least one of the posture of the user, the movements of the user, the activity of the user, the respiration rate of the user and/or the pulse rate of the user.

The device may further comprise a user interface operable by the user or an operator of the device, wherein operation of the user interface causes the device to enter into the calibration mode and to selectively cause the sensor to obtain the first acceleration measurement and the second acceleration measurement.

The first and second acceleration measurements may comprise measurements of proper acceleration experienced by the device.

The information on the amount of rotation of the device relative to the user about the vertical axis of the world reference frame between the first and second measurements being taken may comprise information on an angle $\varphi_p$ between the projections of a basis vector $\beta_m$ in the reference frame of the user onto a horizontal plane H perpendicular to the direction in which gravity acts and the basis vector $\alpha_p$ in the measurement reference frame of the device onto the horizontal plane H for some $m, p \in \{1, 2, 3\}$, where $\beta_m$ and $\alpha_p$ do not lie in the direction of gravity.

The processor can be configured to determine a transformation matrix by:

computing a first coordinate vector d that is orthonormal to the first measurement b;

computing a second coordinate vector f that is orthonormal to b and d;

computing support vectors $s_i$ and radii $r_i$ of the circles $C_1$, $C_2$ and $C_3$ on which the tips of the $\alpha$ basis vectors lie for $i \in \{1, 2, 3\}$;

if $|a_k|=1$ for some $k$ then computing $t_k := \text{sign}(a_k)b$;

computing the p-th column of the transformation matrix; and computing one or more remaining resolvable angles and the corresponding one or more columns of transformation matrix.

The processor can be configured to compute the one or more remaining resolvable angles and the corresponding one or more columns of the transformation matrix as by:

for $i \in \{1,2,3\} \backslash \{p,k\}$ and $j := \{1,2,3\} \backslash \{i,p\}$:

computing the Levi-Civita symbol for the triple (p, i, j);

computing the angle $\varphi_i$ between the projections of the basis vector $\alpha_i$ in the measurement reference frame of the device and the basis vector $\beta_m$ in the reference frame of the user onto the plane H; and computing the corresponding column of the transformation matrix.

The processor can be further configured to estimate the posture of the user, and to use the estimated posture of the user in determining the transformation matrix.

The processor can be configured to estimate the posture of the user by analysing the first measurement of the orientation of the device with respect to the world reference frame or receiving an input from the user or an operator indicating the posture of the user.

The processor can be further configured to cause the display of information associated with the estimated posture of the user for use by the user or an operator in the attachment of the device to the user.

The displayed information may comprise information on permissible rotations of the device between the first and second measurements being taken.

The information on the amount of rotation of the device relative to the user about a vertical axis in the world reference frame between the first and second measurements being taken may be assumed based on the estimated posture of the user.

The information on the amount of rotation of the device relative to the user about a vertical axis in the world reference frame between the first and second measurements being taken may be provided by the user or an operator of the device.

BRIEF DESCRIPTION OF THE DRAWINGS

For a better understanding of the invention, and to show more clearly how it may be carried into effect, reference will now be made, by way of example only, to the accompanying drawings in which.

DETAILED DESCRIPTION OF THE EMBODIMENT

Figure 2:
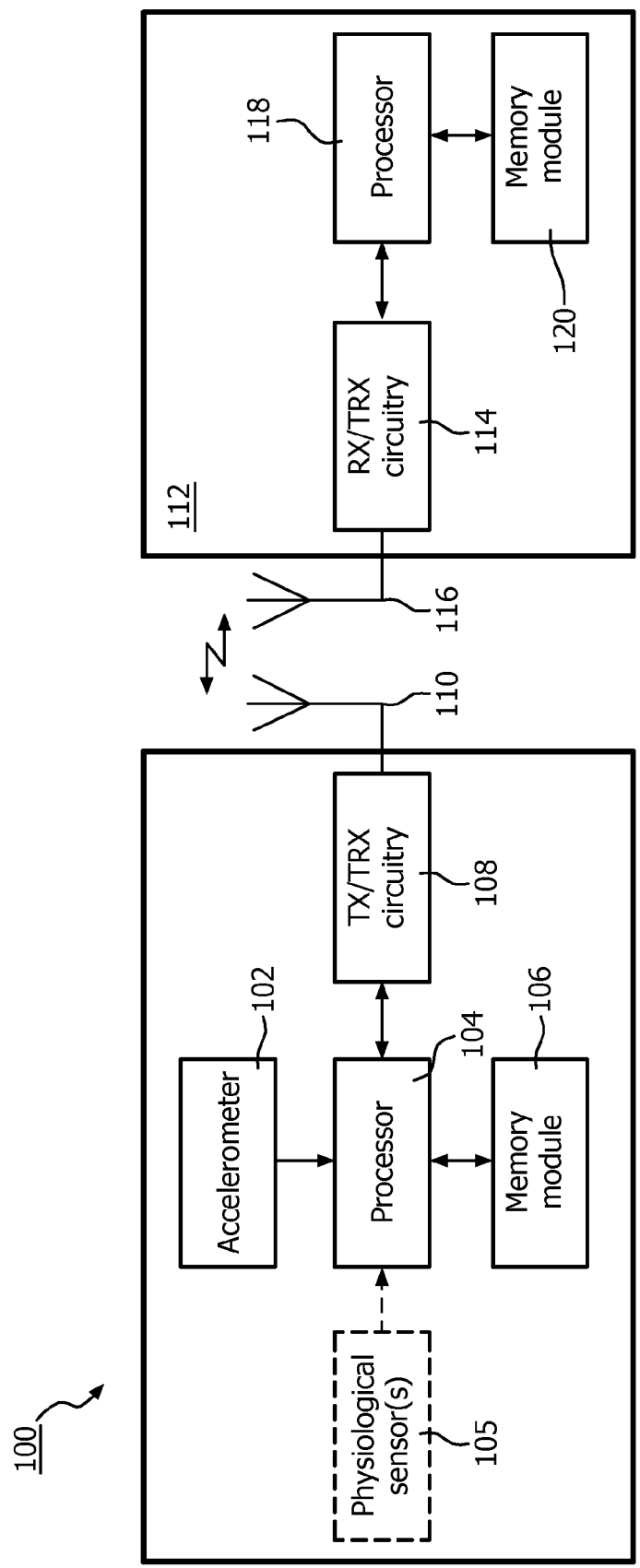
FIG. 2 is a block diagram of a device for monitoring a user according to the invention.

An embodiment of a device 100 for monitoring the movements of a user in accordance with the invention is shown in FIG. 2. The device 100 is adapted to be attached to a part of the body of a user, and will comprise a suitable arrangement for attaching the device 100 to that part of the body (for example a belt or strap). A suitable part of the body to which the device is to be attached may be, for example, the waist, trunk, thorax, pelvis or sternum of the user.

The device 100 comprises a sensor 102 for measuring the proper accelerations (i.e. physical accelerations measurable by an accelerometer) experienced by the device 100, which, assuming that the device 100 is being correctly worn by the user, correspond to the proper accelerations experienced by the user. Any reference to acceleration or measurements of acceleration in this application should be understood as referring to the proper acceleration (i.e. physical accelerations measurable by an accelerometer), not just the rate of change of velocity of the device 100. This sensor 102, for example an accelerometer, outputs the acceleration measurements (signals) to a processor 104 in the device 100. In some embodiments, the accelerometer 102 is a microelectromechanical system (MEMS) accelerometer.

The accelerometer signals obtained from the accelerometer 102 of the device 100 are analysed or processed in the processor 104 during the calibration of the device 100 and when the device is being used to monitor the user to which the device 100 is attached. The measurements obtained from the accelerometer can be used to measure inclination and/or movements, such as the activity of the user (for example the user turning, the user falling, the user exercising, etc), the respiration rate, the pulse rate, or the posture of the user (for example whether the user is upright, supine, prone, laying on their left side, laying on their right side, etc).

In some embodiments, the device 100 may include one or more physiological sensors 105 that measure physiological characteristics of the user. The one or more physiological sensors 105 may include any one or more of a blood pressure monitor, a heart rate monitor, a breathing monitor, a blood oxygen monitor, a weight monitor, or the like.

The device 100 further comprises a memory module 106 that is connected to the processor 104 and that can store the measurements from the accelerometer 102 prior to processing and the results of the processing performed by the processor 104. The memory module 106 can also store the measurements from the one or more physiological sensors 105 (if present). In addition, the memory module 106 may store computer code or program instructions relating to the processing steps to be performed by the processor 104 during the calibration procedure and when determining the posture or orientation of the user, which can be retrieved and executed by the processor 104 as required.

The device 100 further comprises transmitter (TX) or transceiver (TRX) circuitry 108 and an associated antenna 110 that can be used for transmitting the accelerometer measurements or the results of the processing to a base unit 112. The base unit 112 may, for example, be located proximate to the bed of the user or it may, for example, be a computer terminal at a nurse station.

The base unit 112 comprises respective receiver (RX) or transceiver (TRX) circuitry 114 and an antenna 116 for receiving transmissions (such as the accelerometer measurements and/or processing results) from the device 100 and a processor 118 for controlling the operation of the base unit 112.

In an alternative implementation, the device 100 and the base unit 112 may communicate via a wired connection, and antennas 110 and 116 can be omitted, and the circuitry 108 and 114 adapted accordingly.

The base unit 112 also optionally comprises a memory module 120 that is used for storing the information received from the device 100 along with computer code or program instructions relating to the processing steps to be performed by the processor 118 in order to control the operation of the base unit 112.

Although in the embodiment of the invention described herein the processor 104 in the device 100 performs the processing of the accelerometer measurements, it will be appreciated that in an alternative embodiment of the invention, processor 104 in the device 100 can simply transmit the accelerometer measurements to the base unit 112 via the transceiver circuitry 108 and the processing of the accelerometer measurements can be performed by the processor 118 in the base unit 112.

In a further alternative, the processor 104 in the device 100 may perform some initial processing steps on the accelerometer measurements before transmitting the results to the base unit 112 which, for example, completes the processing.

In another alternative, the device 100 may perform the processing steps on the accelerometer measurements and may store the results of the processing locally in the memory module 106 so that it can be retrieved at a later time, after the device 100 has been detached from the user. This alternative would be useful in cases of non-acute or long term monitoring, and for research purposes.

Figure 3:
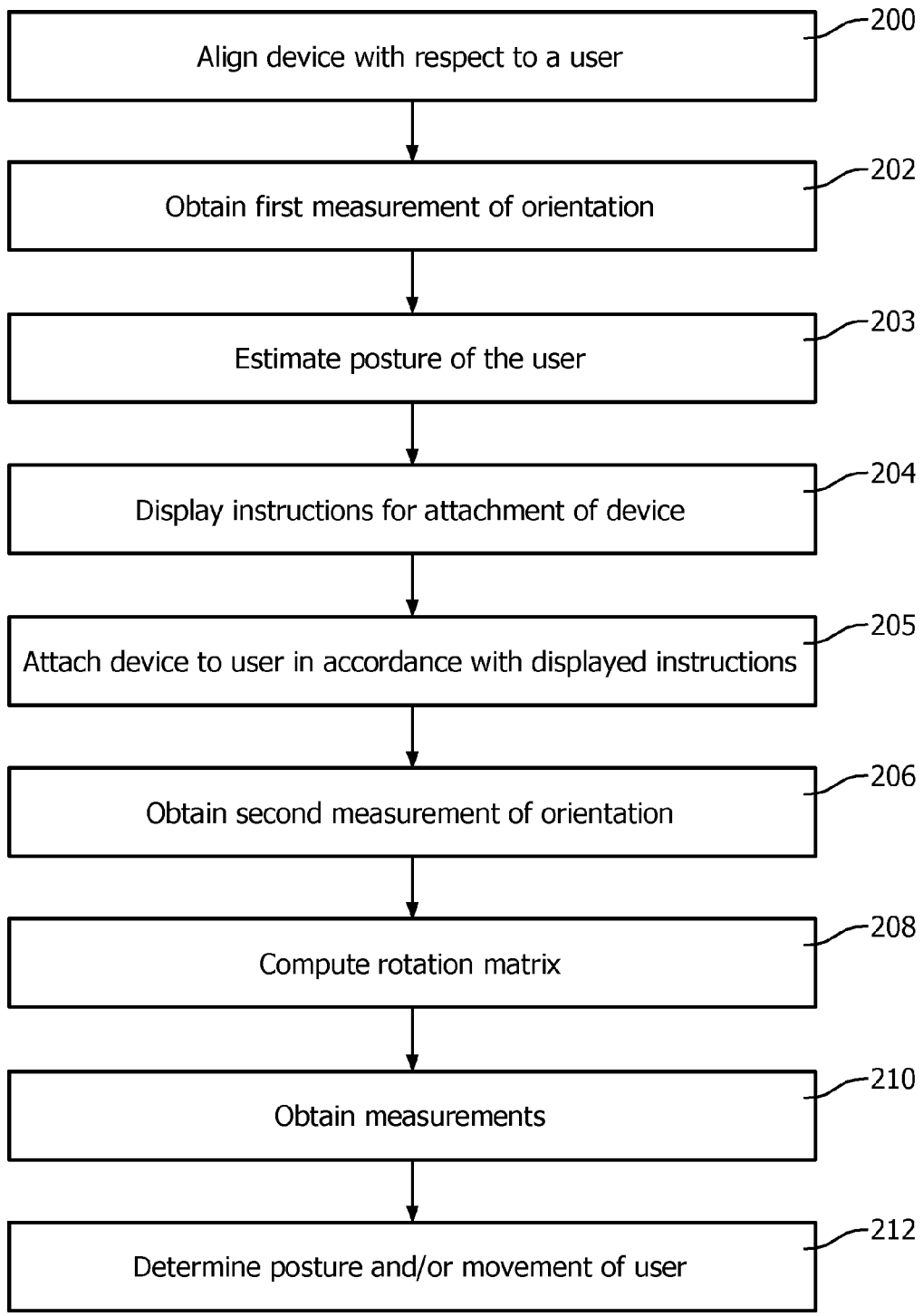
FIG. 3 is a flow chart illustrating a method of calibrating a device that is to be used to monitor the movement of a user according to the invention.

FIG. 3 is a flow chart illustrating some exemplary steps in a method according to an embodiment of the invention. The steps include steps performed in a calibration mode (steps 200 to 208) and steps performed in a measurement mode (steps 210 and 212).

Figure 1:
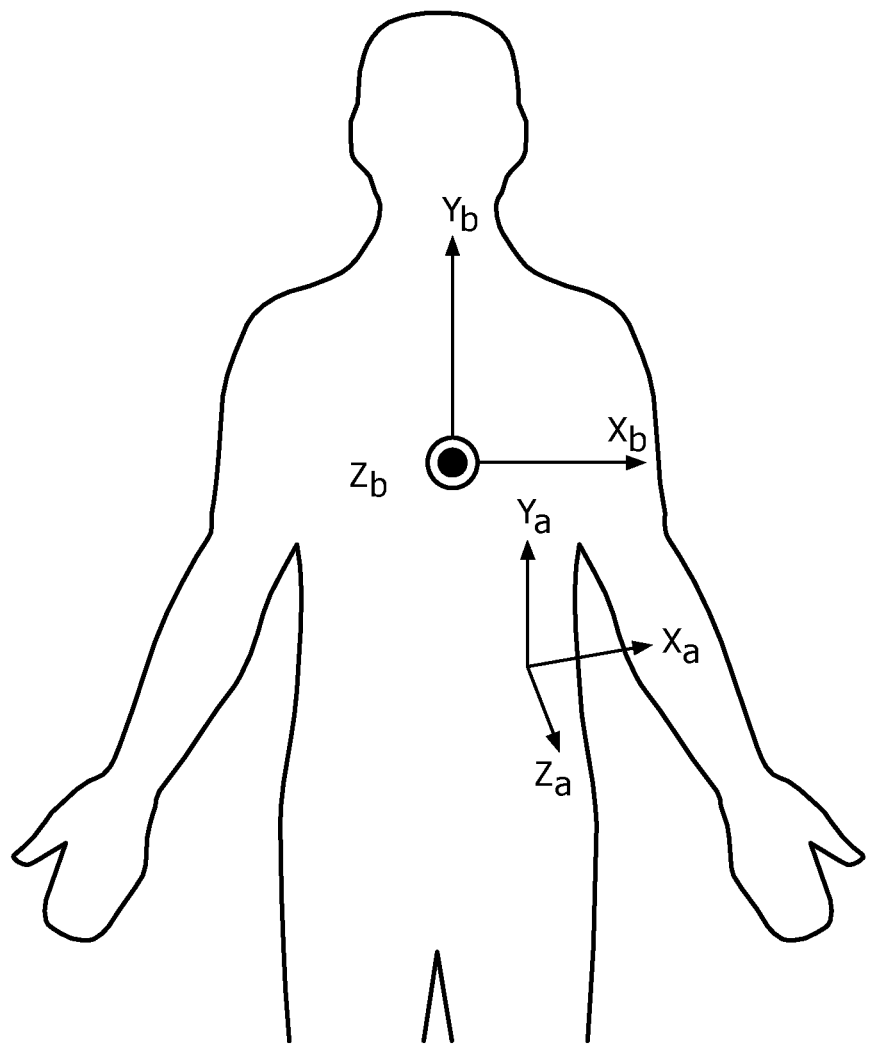
FIG. 1 is a diagram illustrating the reference frames of the user and a device.

The calibration mode (steps 200 to 208) is desirable since, as shown in FIG. 1, the precise orientation of the device 100 and hence accelerometer 102 with respect to the reference frame of the user is unknown. In fact, only the representation of gravity in the reference frame of the device 100 is available as a means of comparison to the reference frame of the user. The difference in orientation between the two reference frames generally comprises three degrees of freedom, while at most two such degrees of freedom can be determined based on the difference in representations of a normalized vector $\bar{c}$, which is the vector in line with gravity and pointing towards the zenith ($\bar{c}$). More specifically, any rotational difference between the two reference frames, which has $\bar{c}$ as a rotation axis, cannot be observed by the sole comparison of the representations of $\bar{c}$ in the respective reference frames.

This problem is summarized mathematically below. For example, let $[\bar{c}]_A$ and $[\bar{c}]_B$ be the coordinate vectors of $\bar{c}$ in the reference frame of the device 100 and the reference frame of the user, respectively. In order to transform the device coordinates $[\bar{c}]_A$ into the body coordinates $[\bar{c}]_B$, it is necessary to determine the coordinate transformation matrix $^B T_A$ which transforms the device coordinates $[\bar{c}]_A$ into the body coordinates $[\bar{c}]_B$, for any possible $[\bar{c}]_A$, and which always gives a unique vector value for $[\bar{c}]_B$. This can be written in equation form as:

$$[\bar{c}]_B = {}^B T_A [\bar{c}]_A \qquad (1)$$

The goal is to determine $^B T_A$ by calibration because then the device coordinates of later measurements can be translated into the corresponding body coordinates.

In general, an orthogonal coordinate transformation matrix has three degrees of freedom and thus can be parameterized by three parameters, $v_1$, $v_2$ and $v_3$. Hence, the coordinate transformation matrix is a function $^B T_A (v_1, v_2, v_3)$, which can be written as:

$$[\bar{c}]_B = {}^B T_A(v_1, v_2, v_3)[\bar{c}]_A \qquad (2)$$

The calibration mode (steps 200 to 208) involves calibrating the device 100 so that the measurements from the accelerometer 102 in reference frame A can be converted into the reference frame (frame B) of the user, thereby allowing the measurements to be used to more accurately determine the posture or movement of the user.

In step 200, which is performed prior to attachment of the device 100 to the user, the device 100 is aligned with respect to a user such that a measurement reference frame of the device 100 substantially or approximately corresponds to the reference frame of the user. This step can be performed by the user themselves, or by an operator, such as a care provider or nurse. The device 100 may have visible markings on the housing of the device 100 indicating the preferred orientation of the device 100 to allow the measurement reference frame of the device 100 to be aligned substantially with the reference frame of the user.

When the device 100 is substantially aligned with the reference frame of the user and the user is upright, the acceleration sensed in the y-direction ($y_a$) should have the largest component of acceleration, since gravity will act in that direction. With the y-axis aligned upwards, the acceleration corresponding to gravity will have a positive sign when the user is standing upright. Similarly, when the user is supine (i.e. lying on their back), acceleration due to gravity will result in the signal along the z-axis being the largest (with a positive sign). When the user is lying on their side, the signal along the x-axis will be largest (with the sign depending on whether the user is lying on their right or left side).

In step 202, which is also performed prior to attachment of the device 100 to the user while the device 100 is substantially aligned with the reference frame of the user, a first measurement of the orientation of the device 100 is obtained using the accelerometer 102. The first measurement comprises a measurement of the acceleration along each of the three axes of the measurement reference frame of the device 100 and should (if the device 100 is motionless) correspond substantially to gravity. In other words, the normalized vector $\bar{c}$ is measured with respect to the device 100 in this step, which gives $[\bar{c}]_B$.

In order to initiate the step of obtaining the first measurement of the orientation, the device 100 may include a suitable user interface, such as a touch screen, button or gesture recognition mechanism (which recognises, for example, a single or double tap) operable by the user or an operator of the device 100 to instruct the accelerometer 102 to obtain the first measurement. Optionally, the first measurement of the orientation of the device 100 obtained from the accelerometer 102 is stored at the memory module 106.

As described in more detail below, in order to determine the correct transformation matrix $^B T_A$, the device 100 requires knowledge of the initial posture of the user (such as supine, reclined at a particular angle or lying on their side). The posture of the user is estimated in step 203. Preferably, the posture of the user is estimated automatically by analysing the first measurement of the orientation of the device (for example by identifying the direction in which gravity is experienced). The device 100 may present an indication of the estimated posture to the user or an operator of the device 100 for confirmation that the correct posture has been estimated. Alternatively, the device 100 can be configured to be only calibrated when the user is in a particular posture (in which case the initial posture is preconfigured in the device 100) or the posture of the user can be input into the device 100 by the user or an operator at some point prior to the device 100 calculating the transformation matrix.

The user or operator can input the information relating to the posture into the device 100 in a number of different ways. For example, the operator or user can select the posture of the user from a list of possible postures presented on a display of the device 100, by adjusting a switch on the device 100 to the appropriate position or by pressing an appropriate button.

Where the posture is manually input into the device 100, the input of the posture of the user is made before the device 100 is attached to the user. This allows the device 100, in step 204, to present information associated with the input posture to the operator or user advising them of the restrictions in place (i.e. permissible rotations between the device's position when the first measurement is taken and the position of the device after attachment to the user). The instructions can be presented on a display of the device 100, printed and illustrated on the housing of the device 100, or displayed on an additional system that is communicating (preferably wirelessly) with the device 100 (e.g. a PC or other display system). The instructions will be explained in more detail later with regard to the specific examples that are described.

It will be appreciated that each restrictive instruction on rotation/orientation can in practice limit the possible attachment locations on the user's body. Specifics of this limitation depend on (1) posture, (2) instruction and (3) body morphologic details of the specific user.

In step 205, the device 100 is attached to the body of the user in accordance with the presented instructions. The presented instructions may optionally include a preferred location on the body of the user to which the device should be attached. The preferred location may be a specific location that is useful for the monitoring that will take place following calibration (for example, vital sign monitoring). Alternatively, the location may be more general (for example, "on the front of the thorax"), which can be useful in order to (1) implicitly limit the allowed rotation of the device between the first and second measurement, (2) ensure a stable attachment location (i.e. not on area with a lot of soft tissue), and/or (3) ensure an attachment location that will be comfortable for the user.

The attachment of the device to the user is achieved using a suitable arrangement for attaching the device 100 to that part of the body (for example, a belt or strap). The predefined location on the body of the user may, for example, be the thorax of the user. More specifically, the predefined location on the body of the user may, for example, be at the left side of the body, approximately at the intersection of the mid-clavicular line and the costal arch.

As a result of the attachment of the device 100 to the user, the orientation of the device 100 may be different from the reference frame of the user, as shown in FIG. 1.

In step 206, a second measurement of the orientation of the device 100 is obtained from the accelerometer 102 once the device 100 is attached to the predefined location on the body of the user. The second measurement comprises a measurement of the acceleration taken along each of the three axes of the reference frame of the device and should, provided the user and the device 100 are substantially motionless, correspond substantially to gravity. This measurement gives $[\bar{c}]_A$.

As before, the user or an operator may initiate the second measurement of the orientation using the user interface. Optionally, the second measurement of the orientation of the device 100 obtained from the accelerometer 102 is stored at the memory module 106.

Since the measurements are taken in only one direction, i.e. only $\bar{c}$, the two coordinate vectors $[\bar{c}]_A$ and $[\bar{c}]_B$, in general only provide information sufficient to resolve at most two degrees of freedom. This leaves one degree of freedom ($v_1$, $v_2$ or $v_3$) in Equation 2, which can be resolved by the processor 104 making use of information on the rotation of the device 100 relative to the user about a vertical axis (in the world coordinate system) between the first and second measurements being taken. This information can be obtained by making certain assumptions and/or applying restrictions to the transformation matrix derivation. The resolvability of the degrees of freedom is dependent on the representation of $\bar{c}$ in the reference frame of the user (i.e. the user's posture during the calibration procedure) and the actual relative orientation between the two reference frames (i.e. the accumulated rotation of the device 100 around a vertical axis (of the world coordinate system) in the period between it being aligned with the reference frame of the user and it being attached to the user's body).

The information can be derived from the restrictions/instructions provided to the user or operator in step 204 (for example, no rotation about the world vertical axis is permitted, so the angle is zero), or an estimate of the angle can be derived from the predefined location to which the device 100 is to be attached or from information input by the user or operator after attachment of the device (for example, an estimate of the rotation about the world vertical axis).

In step 208, the information on the amount of rotation of the device 100 relative to the user about a vertical axis (of the world coordinate system) between the first and second measurements, the measurement of the orientation of the device 100 whilst the device 100 is in alignment with the reference frame of the body of the user ($[\bar{c}]_B$) and the measurement of the orientation of the device 100 while the device 100 is attached to the user ($[\bar{c}]_A$) are used to compute the rotation/transformation matrix. An algorithm for performing step 208 is explained below with reference to FIG. 4.

In particular embodiments, as explained in more detail below, restrictions are placed on the way in which the orientation of the device 100 is permitted to change between the first measurement and second measurement being taken, and the processor 104 assumes such restrictions have been complied with by the user or operator when calculating the transformation matrix. Thus, provided the user or the operator comply with these restrictions, it is possible to compute the complete matrix for transforming subsequent measurements of acceleration obtained by the device 100 into the reference frame of the user.

Step 208 completes the calibration mode and the measurement mode can begin.

In step 210 of the method, measurements are obtained using the accelerometer 102 in the device 100. Then, in step 212, the processor 104 uses the transformation matrix to convert the measurements obtained from the accelerometer 102 into the reference frame of the user, and uses the measurements to determine the posture of the user, or movements of the user, such as the activity of the user, the respiration rate of the user, the pulse rate of the user, etc.

Step 208 will now be described in more detail, with reference to FIGS. 4-7 of the drawings.

In this explanation, the reference frame of the device 100 is denoted by $\alpha \underline{\Delta} \{\alpha_1, \alpha_2, \alpha_3\}$, the reference frame of the user is denoted by $\beta \underline{\Delta} \{\beta_1, \beta_2, \beta_3\}$, and the reference frame of the world is denoted by $\omega \underline{\Delta} \{e_1, e_2, e_3\}$. The $\omega$-, $\alpha$- and $\beta$-reference frame coordinates of $e_3$ are denoted by $\omega$, a and b respectively. b and a correspond to the first and second measurements taken by the device 100 respectively in steps 202 and 206 (i.e. $b=[\bar{c}]_B$ is measured in step in 202 and $a=[\bar{c}]_A$ is measured in step 206). The first and second measurements, denoted b and a respectively (i.e. the $\beta$ and $\alpha$ coordinates of $e_3$), can be written as:

$$b=[b_1,b_2,b_3]^T \text{ and } a=[a_1,a_2,a_3]^T$$

The vector $e_3$ is the vertical axis in the world reference frame, which is the vector in line with gravity and pointing towards the zenith, which has previously been denoted as "$\bar{c}$". The standard basis for the three-dimensional space of component vectors is denoted by $v=\{v_1, v_2, v_3\}$, where $v_1=[1, 0, 0]^T$, $v_2=[0, 1, 0]^T$ and $v_3=[0, 0, 1]^T$.

Also, H denotes the horizontal plane (with respect to the earth), i.e. it is the plane perpendicular to $e_3$, and $P_H(v)$ denotes the projection of an arbitrary spatial vector v onto H. The notations $\alpha_i$ and $\beta_j$ represent the basis vectors of the device $\alpha$ coordinate system and body $\beta$ coordinate system respectively, where $i,j \in \{1, 2, 3\}$ and where the index 1 is used to denote the x-axis, the index 2 is used to denote the y-axis and the index 3 is used to denote the z-axis, in the respective coordinate systems. The tip of each basis vector $\alpha_i$ lies on its corresponding circle $C_i$, where $1 \leq i \leq 3$, with $C_i$ being the circle determined by $b^T t = a_i$ and $\|t\|=1$ expressed in terms of $\beta$ coordinates.

The equation $b^T t = a_i$, where $1 \leq i \leq 3$, represents a plane in three-dimensional space that is horizontal with respect to the world coordinates, i.e. it is orthogonal to the vertical world axis $e_3$ and the gravitational acceleration vector (i.e. it is a plane that is parallel to H).

In order to compute the transformation matrix in step 208, it is necessary to know (e.g. by measurement) or assume the amount of rotation of the device 100 relative to the user about a vertical axis (of the world coordinate system) between the first and second measurements. In mathematical terms, it is necessary to know or assume the angle $\varphi_p$ extending from the projection $P_H(\beta_m)$ of $\beta_m$ onto the horizontal plane H towards the projection $P_H(\alpha_p)$ of $\alpha_p$ onto the horizontal plane, where the direction is defined positive in a counter clockwise direction as observed from the zenith, for some proper indices $m \in \{1, 2, 3\}$ and $p \in \{1, 2, 3\}$ for which $\beta_m$ and $\alpha_p$ do not lie in the direction of the gravitational acceleration vector. At least two such pairs of basis vectors always exist.

Figure 4:
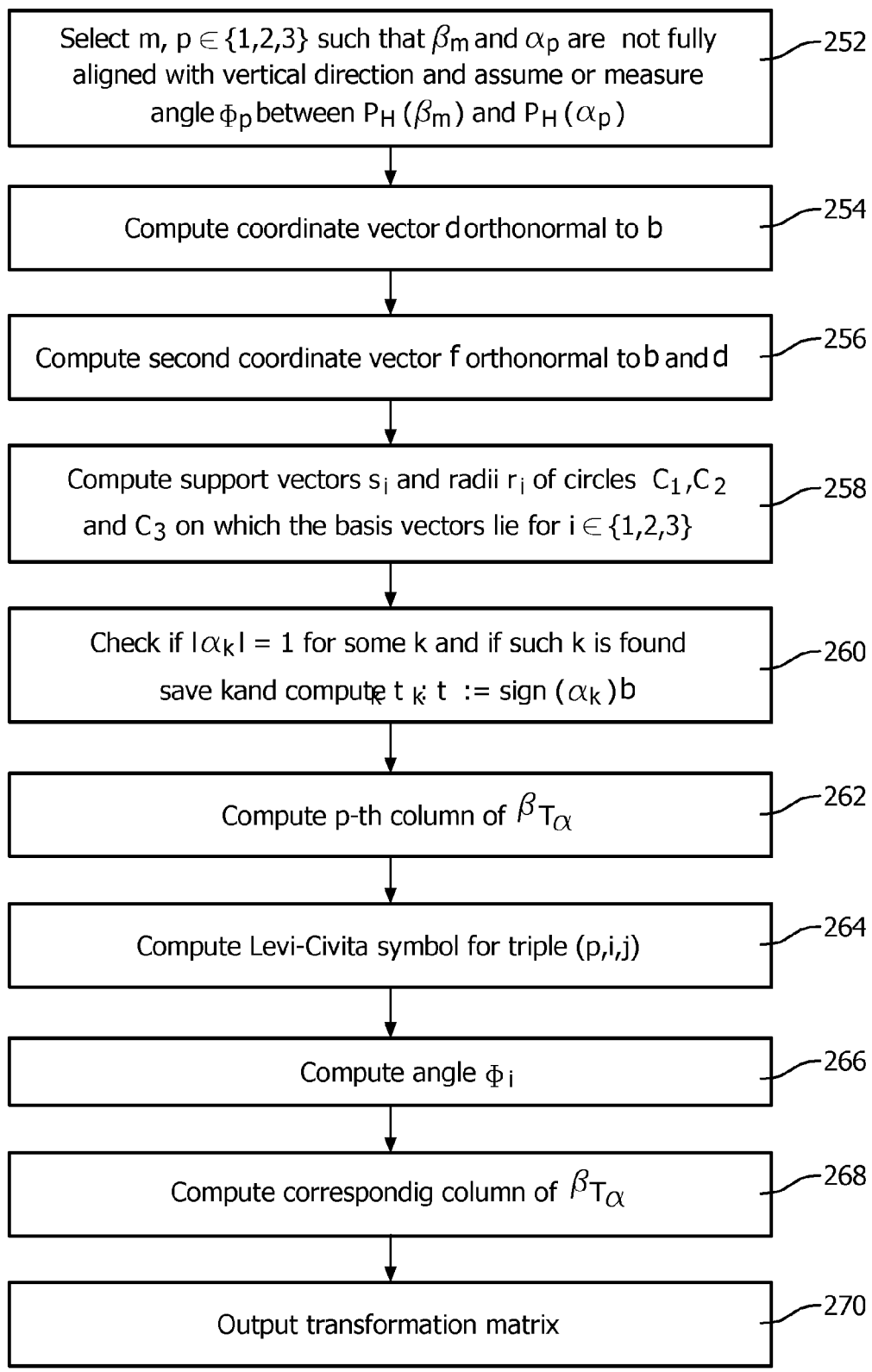
FIG. 4 is a flow chart illustrating an exemplary algorithm for computing a transformation matrix from two acceleration measurements.

In step 252 of FIG. 4, $m, p \in \{1, 2, 3\}$ are selected such that the projections $P_H(\beta_m)$ and $P_H(\alpha_p)$ of the basis vectors $\beta_m$ and $\alpha_p$ respectively onto the horizontal plane H are not fully aligned with the vertical direction. The angle $\varphi_p$ between $P_H(\beta_m)$ and $P_H(\alpha_p)$ is assumed or measured as described above.

In step 254, a coordinate vector d that is orthonormal to b is computed. Preferably d is the coordinate vector corresponding to a projection of a $\beta$ basis vector. In a preferred implementation, d is computed as:

$$d = \frac{1}{\sqrt{1-(b_m)^2}}(v_m - b_m b) \quad (4)$$

In step 256, a second coordinate vector f that is orthonormal to b and d is then computed as:

$$f := b \times d \quad (5)$$

Then, in step 258, support vectors $s_i$ and radii $r_i$ of the circles $C_1$, $C_2$ and $C_3$ on which the tips of the $\alpha$ basis vectors lie are computed from:

$$s_i := a_i b \quad (6)$$

$$r_i := \sqrt{1-(a_i)^2} \quad (7)$$

for each $i \in \{1, 2, 3\}$.

Then, in step 260, it is checked if $|a_k|=1$ for some k and if such k is found, it is saved (k:=i) and $t_k$ is computed as:

$$t_k := \text{sign}(a_k) b \quad (8)$$

In step 262, the p-th column of the transformation matrix $^\beta T_\alpha$ is computed as:

$$t_p := s_p + r_p \cos(\varphi_p) d + r_p \sin(\varphi_p) f \quad (9)$$

Then, in steps 264 to 268, the remaining resolvable angle(s) and the corresponding column(s) of $^\beta T_\alpha$ are computed. In the following, $i \in \{1, 2, 3\} \setminus \{p, k\}$ and $j := \{1, 2, 3\} \setminus \{i, p\}$.

In particular, for $i \in \{1, 2, 3\} \setminus \{p, k\}$ and $j := \{1, 2, 3\} \setminus \{i, p\}$, the Levi-Civita symbol $\epsilon_{pij}$ is computed (in step 264) for the triple (p, i, j) as:

$$\varepsilon_{pij} := \begin{cases} +1 & \text{if } (p, i, j) \in \{(1, 2, 3), (2, 3, 1), (3, 1, 2)\} \\ -1 & \text{if } (p, i, j) \in \{(1, 3, 2), (2, 1, 3), (3, 2, 1)\} \end{cases} \quad (10)$$

Then, in step 266 the angle $\varphi_i$ is computed preferably using:

$$\varphi_i := \varphi_p + \epsilon_{pij} a \tan 2(-a_i a_p, a_j), \quad (11)$$

The notation a tan 2(x, y) is used for the two-argument four quadrant version of the arctangent function with arguments in the indicated order. The two-argument a tan 2(x, y) function computes the arctangent of (i.e. the inverse function of the tangent of) the point (x,y) taking into account the signs of x and y, and it returns the angle in the range $[-\pi, \pi]$.

Then, in step 268, the corresponding i-th column of the transformation matrix $^\beta T_\alpha$ is computed as:

$$t_i := s_i + r_i \cos(\varphi_i) d + r_i \sin(\varphi_i) f \quad (12)$$

Finally, in step 272, the transformation matrix is output as:

$$^\beta T_\alpha = [t_1, t_2, t_3] \quad (13)$$

Figure 5:
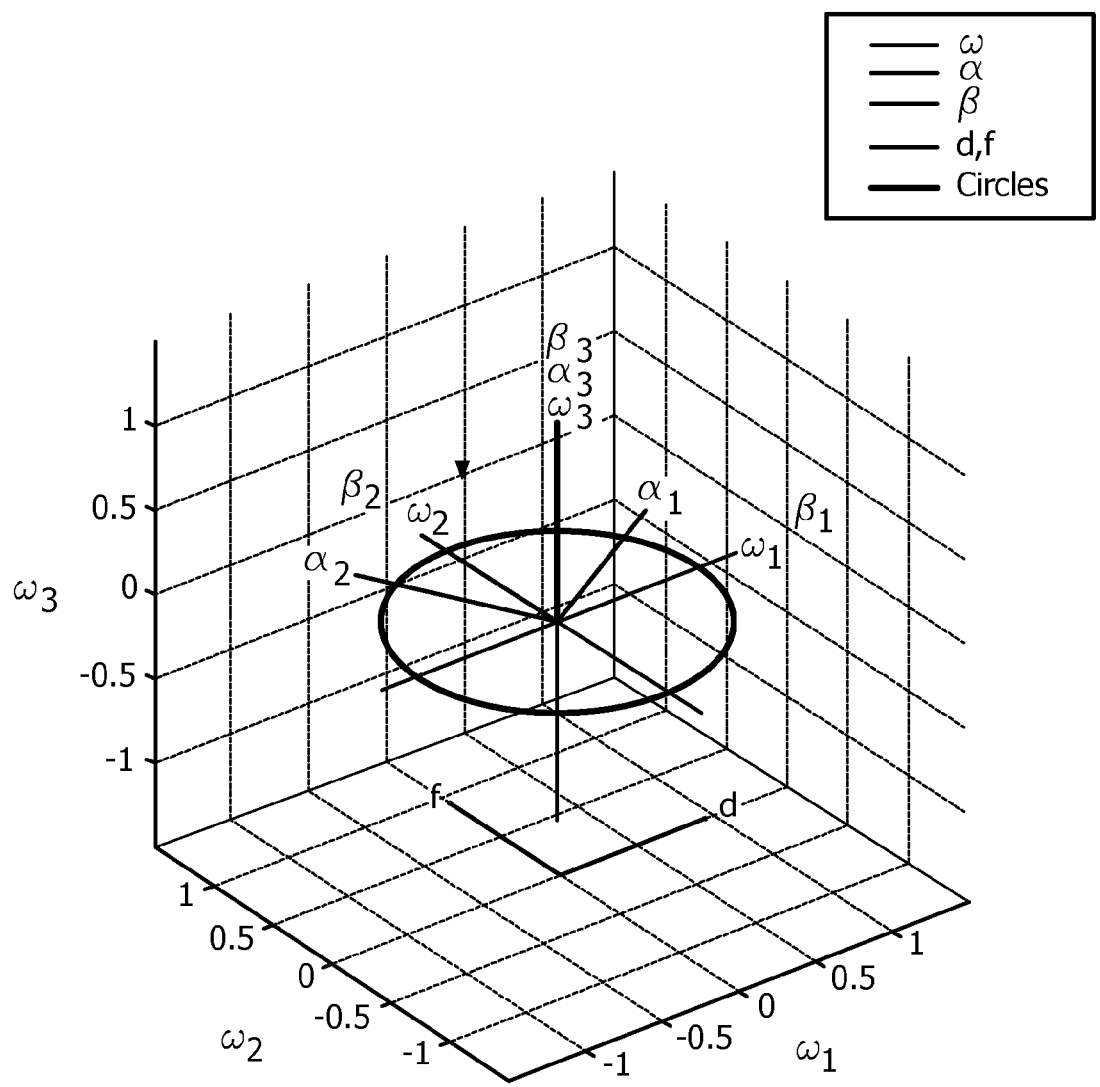
FIG. 5 is a graph illustrating an exemplary set of coordinate systems of the user, the device and the world where the user is lying supine.

Three examples of the application of the above algorithm for calculating a transformation matrix will now be discussed with reference to FIGS. 5 to 7. For simplicity and clarity, without loss of generality, only examples with m=p are described, i.e. $\alpha$ and $\beta$ axes with the same index are always used.

In the first example, the user is lying in a supine position when the device 100 is to be attached to them. FIG. 5 is a graph illustrating the coordinate systems of the user $\beta$, the device $\alpha$ and the world $\omega$ where the user is lying supine.

In this example, suppose that a patient is lying supine and that the (ideal body) $\beta$ coordinate system equals the world $\omega$ coordinate system. Furthermore, suppose that the (actual) a coordinate system is obtained from the world $\omega$ coordinate system by a rotation around the vertical axis by $\pi/6$ radians (in a counter-clockwise direction as observed from the zenith). As can be seen in FIG. 5, $\alpha_3$ and $\beta_3$ (the z-axes of the $\alpha$ and $\beta$ coordinate systems) are fully aligned with the normalized gravitational acceleration vector $e_3$ and it is clear that without knowledge of the rotation around the vertical axis (i.e. $\pi/6$ radians), it would not be possible to figure out the true transformation matrix $^\beta T_\alpha$. Hence, an assumption is made about the rotation angle $\varphi_p$ around the world vertical axis between the projections of the basis vectors $\beta_p$ and $\alpha_p$ onto the horizontal plane H (for this particular example, $P_H(\beta_p)=\beta_p$ and $P_H(\alpha_p)=\alpha_p$ respectively) for $p \neq 3$. It is possible to choose p=1 or p=2, i.e. to compare either the x-axes or the y-axes of the $\alpha$ and $\beta$ systems. In order to find the true transformation matrix $^\beta T_\alpha$, it is assumed that the angle $\varphi_p$ is known. For the current example, this means that it is assumed that $\varphi_1 = \pi/6$ if p=1 is used, i.e. that the angle between the x-axes of the α and β systems is known, or similarly that $\varphi_2=\pi/6$ if p=2 is used, i.e. that the angle between the y-axes of the α and β systems is known. This enables the correct transformation matrix to be found in the scenario where the user is lying supine.

This example will now be described in terms of the inputs to the device by a user or operator (such as an indication of the posture of the user while the measurements are taken in order to place the device in the correct 'mode') as well as the restrictions placed on the change in orientation of the device permitted while the user is in this posture.

A patient is lying supine and a first measurement is obtained in step 202 after aligning the device (reference frame) with the user (reference frame) in step 200. From the obtained first measurement, it is derived that the patient is lying supine (step 203), after which an appropriate strategy is selected (e.g. from a look-up table of postures (or body orientations) vs. strategies) in terms of restrictive instructions. In this example, such a restrictive instruction may be an instruction to ensure that the net rotation of the device around the vertical axis between the obtained first measurement and the second measurement, which will be obtained subsequent to attachment of the device 100 to the user, equals a predetermined value (e.g. π/6 as above, or zero). To facilitate practical execution of this instruction, two lines may be drawn (or electronically displayed) on a side of the device that is in the horizontal plane during the first measurement. The first line would preferably correspond to the device y-axis and the second line would cross the first line with an angle equal to the predetermined value (π/6 in this example). As the device y-axis is aligned with the body y-axis during the first measurement, the user or an operator needs to ensure that the second line is aligned with the body y-axis during the step of obtaining the second measurement, step 206. In this particular example, only the projection of the second line onto the horizontal plane needs to be aligned with the body y-axis since the projection is equal to the line itself where the user is lying supine. With this instruction, it is subsequently assumed that the actual rotation around the vertical axis is in fact equal to the predetermined value. After the device has been attached to the user in step 205 while complying with the instruction, a second measurement is obtained in step 206, completing the set of required inputs for the algorithm to determine the full transformation matrix in step 208.

In the second example, the user is lying in a reclined position at π/6 radians with respect to the horizontal plane when the device 100 is to be attached to them. FIG. 6 is a graph illustrating the coordinate systems of the user β, the device α and the world ω where the user is lying reclined at π/6 radians with respect to the horizontal plane. Suppose that the (ideal body) β coordinate system is obtained from the world coordinate system by a rotation around the first world axis $\omega_1$ (the x-axis) by π/6 radians. Furthermore, suppose that the (actual) a coordinate system is obtained from the world coordinate system by a rotation around the first world axis $\omega_1$ by π/6 radians, followed by another rotation around the new axis with index 2 (the y-axis) by π/4 radians.

Figure 6:
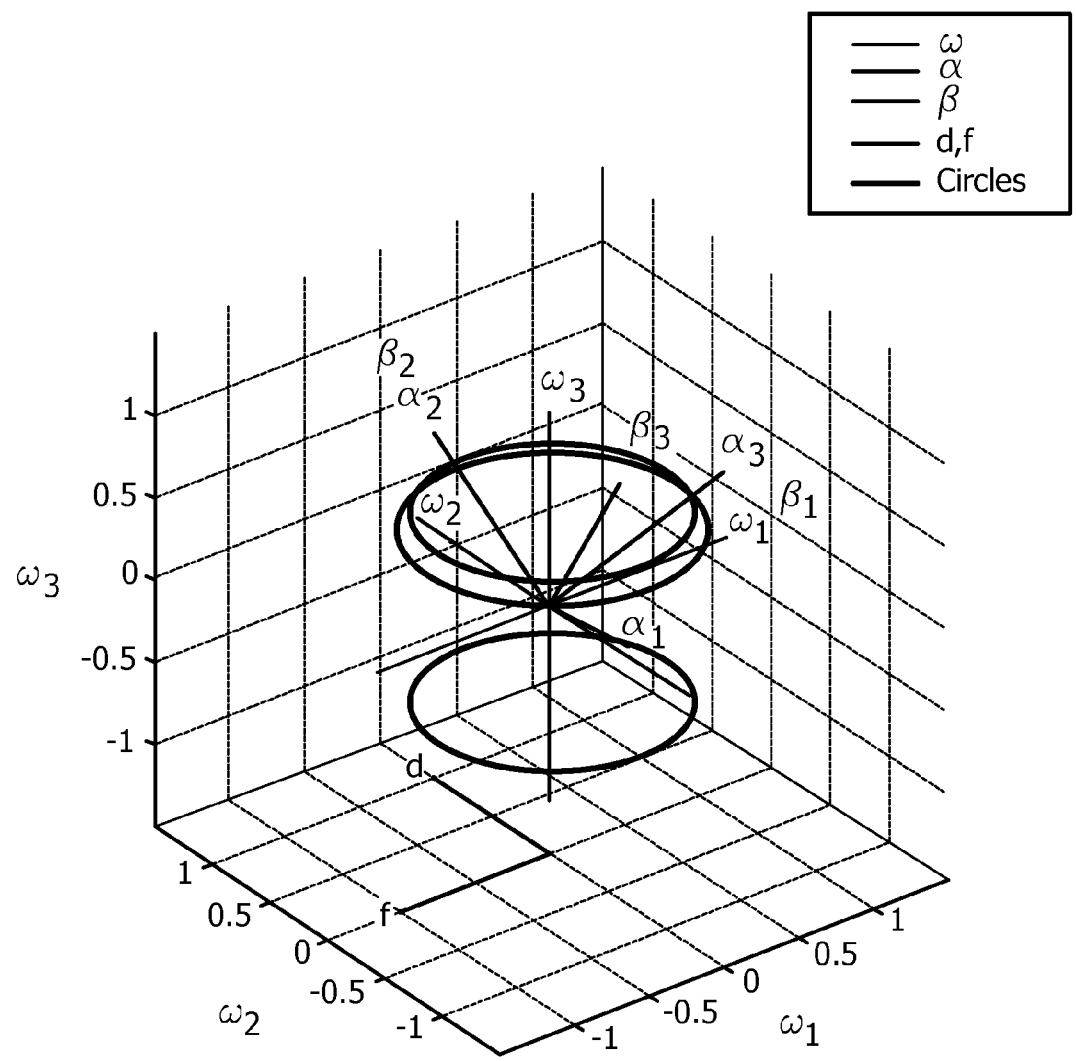
FIG. 6 is a graph illustrating an exemplary set of coordinate systems of the user, the device and the world where the user is lying reclined at $\pi/6$ radians with respect to the horizontal plane.
Figure 7:
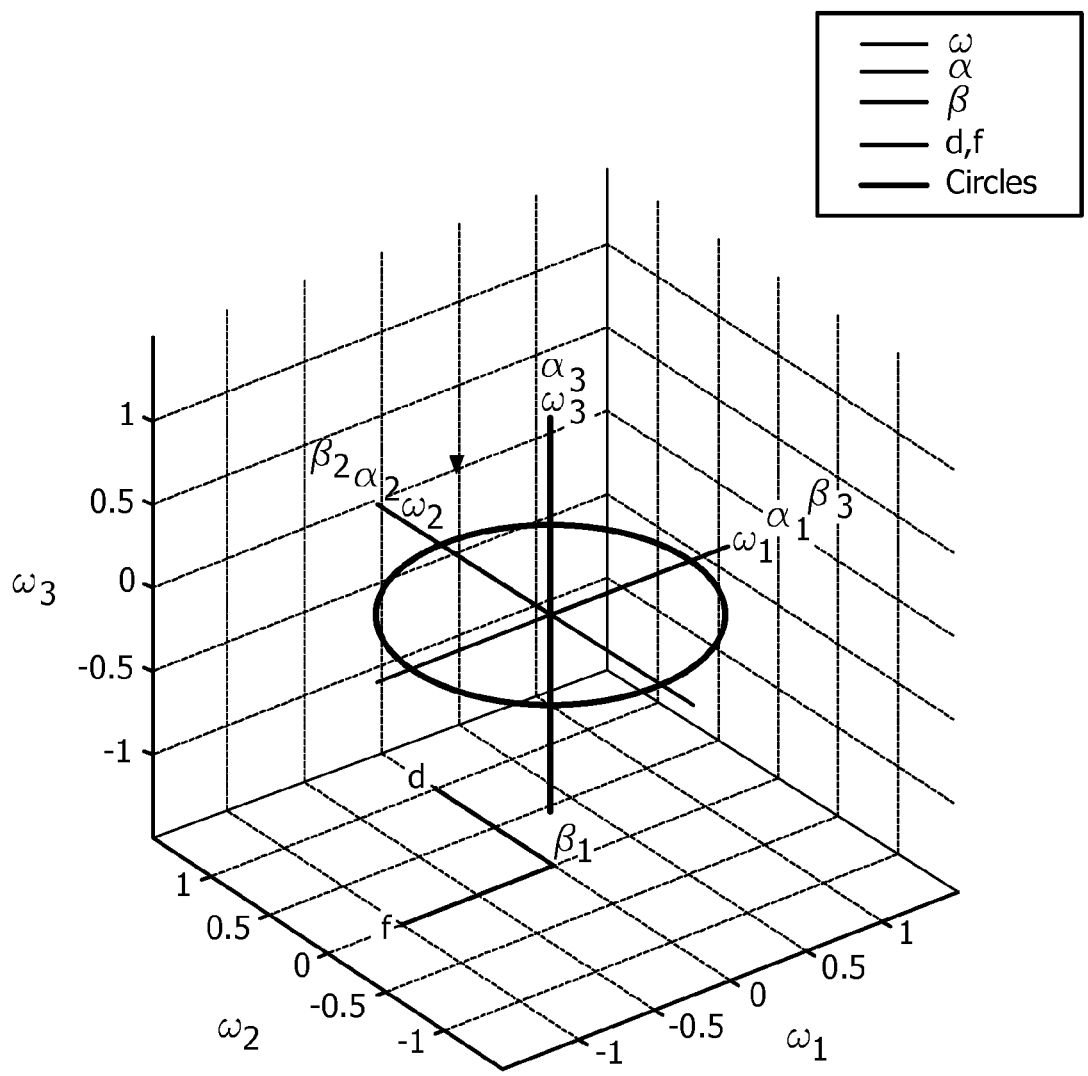
FIG. 7 is a graph illustrating the coordinate systems of the user, the device and the world where the user is lying on their left side.

As evident from FIG. 6, none of the axes are fully aligned with the normalized gravitational acceleration vector $e_3$ and, in principle, any p∈{1, 2, 3} could be used. However, with the sequence of rotations defining the α basis, the basis vectors $\alpha_2$ and $\beta_2$ (the y-axes of the device and body coordinate systems respectively) remain in the same vertical plane spanned by the second world axis $\omega_2$ and the third world axis $\omega_3$. Thus, the same holds for the projections of the basis vectors $\alpha_2$ and $\beta_2$ onto the horizontal plane. Hence, it is the easiest and most practical to use p=2 with the angle $\varphi_2$ between the projections of the basis vectors $\beta_2$ and $\alpha_2$ onto the horizontal plane equal to zero radians. This enables the correct transformation matrix to be found in the scenario where the user is lying reclined at π/6 radians with respect to the horizontal plane. In practice, when the user is reclined at π/6 radians with respect to the horizontal plane, the operator could be instructed by the device 100 to keep the y-axes of the device α and body β coordinate systems in the same vertical plane.

This example will now be described in terms of the inputs to the device by a user or operator (such as an indication of the posture of the user while the measurements are taken in order to place the device in the correct 'mode') as well as the restrictions placed on the change in orientation of the device permitted while the user is in this posture.

A patient is lying reclined and a first measurement is obtained in step 202 after aligning the device (reference frame) with the user (reference frame) in step 200. From the obtained first measurement, it is derived that the patient is lying reclined (step 203), after which an appropriate strategy is selected in step 204 (e.g. from a look-up table of postures (or body orientations) vs. strategies) in terms of restrictive instructions. In this example, such a restrictive instruction may be an instruction to ensure that the net rotation of the device around the vertical axis between the obtained first measurement and the second measurement, which will be obtained subsequent to attachment of the device 100 to the user, equals zero, i.e. a line indicating the device y-axis, drawn on a side of the device that is parallel to the device x-y-plane, is kept at a constant direction (more specifically: the direction of the body y-axis) in terms of components/projections in the horizontal plane. With this instruction it is subsequently assumed that the 'known angle' as mentioned in the description above is in fact equal to zero. After the device has been attached to the user in step 205 while complying with the instruction, a second measurement is obtained in step 206, completing the set of required inputs for the algorithm to determine the full transformation matrix in step 208.

In the third example, the user is lying on their left side when the device 100 is to be attached to them. FIG. 7 is a graph illustrating the coordinate systems of the user β, the device α and the world ω where the user is lying on their left side. Suppose that the (ideal body) β coordinate system is obtained from the world coordinate system by a rotation of π/2 radians around the second world axis $\omega_2$ (the y-axis of the world coordinate system). Furthermore, suppose that the (actual) device α coordinate system is equal to the world coordinate system (for example, by the device being mounted on the right side of the user with the y-axis of the device pointing towards the head of the user and the z-axis of the device pointing towards the zenith). The x-axis of the body coordinate system $\beta_1$ and the z-axis of the device coordinate system $\alpha_3$ are fully aligned with the normalized gravitational acceleration vector and thus it is necessary to use p=2. As can be seen from FIG. 7, the angle $\varphi_2$ between the projections of the basis vectors $\beta_2$ and $\alpha_2$ onto the horizontal plane is equal to zero radians. This enables the correct transformation matrix to be found in the scenario where the user is lying on their left side.

This example will now be described in terms of the inputs to the device by a user or operator (such as an indication of the posture of the user while the measurements are taken in order to place the device in the correct 'mode') as well as the restrictions placed on the change in orientation of the device permitted while the user is in this posture.

A patient is lying on their left side and a first measurement is obtained in step 202 after aligning the device (reference frame) with the user (reference frame) in step 200. From the obtained first measurement, it is derived that the patient is lying on their left side (step 203), after which an appropriate strategy is selected (e.g. from a look-up table of postures (or body orientations) vs. strategies) in step 204 in terms of restrictive instructions. In this example, such a restrictive instruction may be an instruction to ensure that the net rotation of the device around the vertical axis between the obtained first measurement and the second measurement, which will be obtained subsequent to attachment of the device 100 to the user, equals zero, i.e. a line indicating the device y-axis, drawn on a side of the device that is parallel to the device x-y-plane, is kept at a constant direction (more specifically: the direction of the body y-axis) in terms of components/projections in the horizontal plane. With this instruction it is subsequently assumed that the 'known angle' as mentioned in the description above is in fact equal to zero. After the device has been attached to the user in step 205 while complying with the instruction, a second measurement is obtained in step 206, completing the set of required inputs for the algorithm to determine the full transformation matrix in step 208.

It will be appreciated that the user can be in other postures to those described above. For example, the user may be lying in a reclined position at another angle (i.e. any angle between 0 and π/2 radians. In such a case, the scenario would be the same as the scenario described above where the user is lying reclined at π/6 radians with respect to the horizontal plane, except that the (ideal body) β coordinate system and the (actual) α coordinate system would be obtained from the world coordinate system by different rotations around the world axes.

There is therefore provided a device for monitoring a user and a method for calibrating the device that can be performed without any active involvement or support from the user being monitored with the device such that accurate readings can subsequently be obtained from the device.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method of calibrating a device that is to be attached to a user and used to monitor the user, the method comprising:
    (i) prior to attachment of the device to the user, aligning the device with respect to the user to substantially align a measurement reference frame of the device with a reference frame of the user and obtaining a first measurement of an orientation of the device with respect to a world reference frame using the device;
    (ii) estimating a posture of the user;
    (iii) after attachment of the device to the user, obtaining a second measurement of the orientation of the device with respect to the world reference frame using the device; and
    (iv) with at least one electronic processor, determining a transformation matrix for use in transforming subsequent measurements obtained by the device into the reference frame of the user, the transformation matrix being calculated using the obtained first and second measurements, the estimated posture of the user, and information on an amount of rotation of the device relative to the user about a vertical axis in the world reference frame between (i) and (ii).

2. The method according to claim 1, wherein the information on the amount of rotation of the device relative to the user about the vertical axis of the world reference frame between (i) and (iii) comprises:
    information on an angle $\varphi_p$ between projections of a basis vector $\beta_m$ in the reference frame of the user onto a horizontal plane H perpendicular to a direction in which gravity acts and a basis vector $\alpha_p$ in the measurement reference frame of the device onto the horizontal plane H for some $m, p \in \{1, 2, 3\}$, where $\beta_m$ and $\alpha_p$ do not lie in the direction of gravity.

3. The method according to claim 2, wherein determining the transformation matrix comprises:
    with the at least one electronic processor, computing a first coordinate vector d that is orthonormal to a first measurement b;
    with the at least one electronic processor, computing a second coordinate vector f that is orthonormal to b and d;
    with the at least one electronic processor, computing support vectors $s_i$ and radii $r_i$ of the circles $C_1$, $C_2$ and $C_3$ on which tips of the α basis vectors lie for $i \in \{1, 2, 3\}$;
    if $|a_k|=1$ for some k then, with the at least one electronic processor, computing $t_k := \text{sign}(a_k)b$;
    with the at least one electronic processor, computing the p-th column of the transformation matrix; and
    with the at least one electronic processor, computing one or more remaining resolvable angles and a corresponding one or more columns of transformation matrix.

4. The method according to claim 3, wherein computing one or more remaining resolvable angles and the corresponding one or more columns of the transformation matrix comprises, for $i \in \{1, 2, 3\} \setminus \{p, k\}$ and $j := \{1, 2, 3\} \setminus \{i, p\}$:
    with the at least one electronic processor, computing a Levi-Civita symbol for a triple (p, i, j);
    with the at least one electronic processor, computing an angle $\varphi_i$ between the projections of the basis vector $\alpha_i$ in the measurement reference frame of the device and the basis vector $\beta_m$ in the reference frame of the user onto the plane H; and
    with the at least one electronic processor, computing the corresponding column of the transformation matrix.

5. The method according to claim 1, wherein estimating the posture of the user comprises:
    with the at least one electronic processor, analyzing the first measurement of the orientation of the device with respect to the world reference frame or receiving an input from the user or an operator indicating the posture of the user.

6. The method as claimed in claim 1, the method further comprising:
displaying information associated with the estimated posture of the user for use by the user or an operator in the attachment of the device to the user.

7. The method as claimed in claim 6, wherein the displayed information comprises information on permissible rotations of the device between (i) and (iii).

8. The method as claimed in claim 1, further comprising:
with the at least one electronic processor, determining the information on the amount of rotation of the device relative to the user about the vertical axis in the world reference frame between (i) and (iii) is based on the estimated posture of the user.

9. The method as claimed in claim 1, wherein the information on the amount of rotation of the device relative to the user about the vertical axis in the world reference frame between (i) and (iii) is provided by the user or an operator of the device.

10. The method as claimed in claim 1, further comprising:
obtaining further measurements using the device;
with the at least one electronic processor, converting the obtained further measurements into the reference frame of the user using the transformation matrix; and
with the at least one electronic processor, using the converted obtained further measurements, determining at least one of a posture of the user, movements of the user, an activity of the user, a respiration rate of the user and a pulse rate of the user.

11. A non-transitory computer readable medium comprising a plurality of program code portions for carrying out a method executed by a suitable computer or processor, the method comprising:
prior to attachment of a device to a user, obtaining a first acceleration measurement as an indication of the orientation of the reference frame of the user with respect to a world reference frame prior to attachment of the device to the user;
following attachment of the device to the user, obtaining a second acceleration measurement as a measurement of the orientation of the device with respect to a world reference frame; and
with at least one electronic processor, calculating a transformation matrix for use in transforming subsequent acceleration measurements obtained by the device into the reference frame of the user, the transformation matrix being calculated using the obtained first and second measurements and information on the amount of rotation of the device relative to the user about a vertical axis of the world reference frame between the first and second measurements being taken; wherein calculating the transformation matrix comprises:
with the at least one electronic processor, computing a first coordinate vector d that is orthonormal to a first measurement b;
with the at least one electronic processor, computing a second coordinate vector f that is orthonormal to b and d;
with the at least one electronic processor, computing support vectors $s_i$ and radii $r_i$ of the circles $C_1$, $C_2$ and $C_3$ on which tips of the α basis vectors lie for i∈{1, 2, 3};
if $|a_k|=1$ for some k then, with the at least one electronic processor, computing $t_k$=sign $(a_k)$b;

with the at least one electronic processor, computing the p-th column of the transformation matrix; and
with the at least one electronic processor, computing one or more remaining resolvable angles and a corresponding one or more columns of transformation matrix.

12. The non-transitory computer readable medium according to claim 11, wherein computing one or more remaining resolvable angles and the corresponding one or more columns of the transformation matrix comprises, for i∈{1, 2, 3\{p, k}} and j={1, 2, 3\{i, p}}:
with the at least one electronic processor, computing a Levi-Civita symbol for a triple (p, i, j);
with the at least one electronic processor, computing an angle $\varphi_i$ between the projections of the basis vector $\alpha_i$ in the measurement reference frame of the device and the basis vector $\beta_m$ in the reference frame of the user onto the plane H; and
with the at least one electronic processor, computing the corresponding column of the transformation matrix.

13. A device for monitoring a user, the device being suitable for attachment to a user, the device comprising:
a sensor configured to measure accelerations; and
at least one electronic processor programmed to process the acceleration measurements by operations including,
when the device is operating in a calibration mode:
using a first acceleration measurement as an indication of an orientation of a reference frame of the user with respect to a world reference frame obtained prior to attachment of the device to the user and a second acceleration measurement as a measurement of the orientation of the device with respect to the world reference frame following attachment of the device to the user,
calculating a transformation matrix for use in transforming subsequent acceleration measurements obtained by the device into the reference frame of the user, the transformation matrix being calculated using the obtained first and second measurements and information on the amount of rotation of the device relative to the user about a vertical axis of the world reference frame between the first and second measurements being taken; and
further calculating the transformation matrix with an estimated posture of the user.

14. The device as claimed in claim 13, wherein the at least one electronic processor is further programmed to convert further acceleration measurements obtained by the sensor into the reference frame of the user with the calculated transformation matrix.

15. The device as claimed in claim 13, further comprising:
a user interface operable by the user or an operator of the device, wherein operation of the user interface causes the device to enter into the calibration mode and to selectively cause the sensor to obtain the first acceleration measurement and the second acceleration measurement.

16. The device according to claim 13, wherein the at least one electronic processor is further programmed to:
compute a first coordinate vector d that is orthonormal to the first acceleration measurement b;
compute a second coordinate vector f that is orthonormal to b and d;

compute support vectors $s_i$ and radii $r_i$ of the circles $C_1$, $C_2$ and $C_3$ on which tips of the α basis vectors lie for i∈{1, 2, 3};

if $|a_k|=1$ for some k then compute $t_k$=sign $(a_k)$b;

compute the p-th column of the transformation matrix; and compute one or more remaining resolvable angles and a corresponding one or more columns of transformation matrix.

17. The device according to claim 16, wherein computing one or more remaining resolvable angles and the corresponding one or more columns of the transformation matrix comprises, for i∈{1, 2, 3\{p, k}} and j={1, 2, 3\{i, p}}; and the at least one electronic processor is further programmed to:

compute a Levi-Civita symbol for a triple (p, i, j);

compute an angle $\varphi_i$ between the projections of the basis vector $\alpha_i$ in the measurement reference frame of the device and the basis vector $\beta_m$ in the reference frame of the user onto the plane H; and compute the corresponding column of the transformation matrix.

18. The device according to claim 13, wherein the at least one electronic processor is further programmed to:

obtain the estimated posture of the user prior to attachment of the device to the user.

* * * * *